United States Patent
Matsumoto (10) Patent No.: US 11,647,979 B2
(45) Date of Patent: May 16, 2023

(54) ULTRASOUND DIAGNOSTIC APPARATUS AND METHOD OF CONTROLLING ULTRASOUND DIAGNOSTIC APPARATUS

(71) Applicant: FUJIFILM Corporation, Tokyo (JP)

(72) Inventor: Tsuyoshi Matsumoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 112 days.

(21) Appl. No.: 17/145,467

(22) Filed: Jan. 11, 2021

(65) Prior Publication Data

US 2021/0128101 A1 May 6, 2021

Related U.S. Application Data (63) Continuation of application No. PCT/JP2019/026022, filed on Jul. 1, 2019.

(30) Foreign Application Priority Data

Aug. 27, 2018 (JP) .............................. JP2018-158383

(51) Int. Cl.
*A61B 8/08* (2006.01)
*A61B 8/00* (2006.01)

(52) U.S. Cl.
CPC ................ *A61B 8/08* (2013.01); *A61B 8/403* (2013.01); *A61B 8/4254* (2013.01); *A61B 8/4444* (2013.01); *A61B 8/461* (2013.01)

(58) Field of Classification Search
CPC ......... A61B 8/08; A61B 8/403; A61B 8/4254; A61B 8/4444; A61B 8/461; A61B 8/488; A61B 8/0891
See application file for complete search history.

(56) References Cited

U.S. PATENT DOCUMENTS

2008/0269605 A1  10/2008 Nakaya
2017/0296139 A1  10/2017 Giaya et al.

FOREIGN PATENT DOCUMENTS

JP  2008-272025 A  11/2008
JP  2013-158348 A  8/2013

OTHER PUBLICATIONS

Young Hwang, "Doppler ultrasonography of the lower extremity arteries: anatomy and scanning guidelines", published on Jan. 18, 2017 (Year: 2017).*

(Continued)

*Primary Examiner* — Keith M Raymond
*Assistant Examiner* — Fikirte (Fiki) T Ashine
(74) *Attorney, Agent, or Firm* — Studebaker & Brackett PC (57) ABSTRACT

An ultrasound diagnostic apparatus (1), which performs a compression test with respect to at least two points of a popliteal vein and a common femoral vein of a subject, includes an ultrasound probe (15), an image acquisition unit (8) that acquires an ultrasound image by transmitting an ultrasound beam toward the subject from the ultrasound probe (15), a vein detection unit (9) that detects the popliteal vein included in the ultrasound image, and an operation guiding unit (10) that guides a user, in a case where the compression test of the popliteal vein is performed, to operate the ultrasound probe such that the ultrasound probe (15) is positioned at a position in which only one popliteal vein is included in the ultrasound image based on the number of the popliteal veins detected by the vein detection unit (9).

11 Claims, 7 Drawing Sheets

(56) References Cited

OTHER PUBLICATIONS

Alexander et al., "Puncture of the popliteal artery using a Doppler-equipped (SMART) needle in transpopliteal interventions", published on Oct. 2002. (Year: 2002).*
Ji Young et al, "Doppler ultrasonography of the lower extremity arteries anatomy and scanning guidelines" (Year: 2017).*
Alexander et al. , "Puncture of the popliteal artery using a Doppler-equipped (SMART) needle in trans popliteal interventions" (Year: 2003).*
The extended European search report issued by the European Patent Office dated Sep. 23, 2021, which corresponds to European Patent Application No. 19854914.9-1126 and is related to U.S. Appl. No. 17/145,467.
International Search Report issued in PCT/JP2019/026022; dated Sep. 3, 2019.
Nternational Preliminary Report on Patentability and Written Opinion issued in PCT/JP2019/026022; dated Mar. 2, 2021.
Kano, Kenichi, Deep vein thrombosis (DVT)—only 2 things to see!—), May 2018, vol. 100, No. 5, pp. 575-578, (The Journal of Therapy) , non-official translation.

* cited by examiner

ULTRASOUND DIAGNOSTIC APPARATUS AND METHOD OF CONTROLLING ULTRASOUND DIAGNOSTIC APPARATUS

CROSS-REFERENCE TO RELATED APPLICATIONS

This application is a Continuation of PCT International Application No. PCT/JP2019/026022 filed on Jul. 1, 2019, which claims priority under 35 U.S.C § 119(a) to Japanese Patent Application No. 2018-158383 filed on Aug. 27, 2018. Each of the above application(s) is hereby expressly incorporated by reference, in its entirety, into the present application.

BACKGROUND OF THE INVENTION

1. Field of the Invention

The present invention relates to an ultrasound diagnostic apparatus and a method of controlling an ultrasound diagnostic apparatus, and particularly, to an ultrasound diagnostic apparatus and a method of controlling an ultrasound diagnostic apparatus that are used for a compression test of a popliteal vein of a subject.

2. Description of the Related Art

In the related art, an ultrasound diagnostic apparatus has been known as an apparatus that obtains an image of the inside of a subject. Generally, the ultrasound diagnostic apparatus comprises an ultrasound probe provided with an oscillator array in which a plurality of elements are arranged. In a state where the ultrasound probe is brought into contact with a body surface of the subject, an ultrasound beam is transmitted from the oscillator array toward the inside of the subject, ultrasound echoes from the subject are received by the oscillator array, and element data are acquired. Moreover, the ultrasound diagnostic apparatus processes the obtained element data electrically, and generates an ultrasound image for a relevant part of the subject.

It is generally performed that a blood vessel of the subject is observed using such an ultrasound diagnostic apparatus, and the presence or absence of a thrombus in the blood vessel is inspected. As a disease related to the thrombus in the blood vessel, for example, a so-called deep vein thrombosis (DVT) is known. The DVT is a disease that a thrombus occurs in a deep vein, and often occurs in a lower thigh.

Although a normal deep vein in which the thrombus is not present is easily deformed by compression, the deep vein in which the thrombus occurs is not easily deformed by the compression. Therefore, as a method of inspecting the DVT that occurs in the lower thigh using the ultrasound diagnostic apparatus, for example, so-called compression test method of observing a cross section of the compressed deep vein while compressing the deep vein having a concern that the DVT may occur is known.

For the ultrasound diagnostic apparatus, various measures are made in order to accurately perform such a compression test. For example, JP2008-272025A discloses an ultrasound diagnostic apparatus that, in a case of a compression test of the deep vein, recognizes the deep veins for the acquired frames to calculate a vein diameter, and displays the ultrasound image of the frame in which the vein diameter is maximum and the ultrasound image of the frame in which the vein diameter is minimum on a display unit side by side.

SUMMARY OF THE INVENTION

As a method of quickly detecting DVT occurring in the lower thigh of the subject, a so-called two-point compression method is known in which a compression test is performed with respect to only two points of the popliteal vein and the common femoral vein. The popliteal vein is generally observed as one blood vessel in a case where the ultrasound probe is brought into contact with the back of the knee of the subject, but in some cases, the popliteal vein branches to an upper side of the back of the knee depending on the subject, and two small blood vessels are observed in a case where the ultrasound probe is brought into contact with the back of the knee of the subject.

In general, the larger thrombus is likely to occur as the vein is thicker, and in a case where the thrombus is peeled off from the inner wall of the vein and flows to the central side of the vein, pulmonary embolism is likely to be caused, and thus it is desirable that the compression test is performed above the branched part of the vein. However, for example, a less skilled user may perform the compression test without moving the position of the ultrasound probe from the back of the knee, even in a case where the vein branches to an upper side of the back of the knee. In such a case, even with the ultrasound diagnostic apparatus disclosed in JP2008-272025A, there is a problem that an appropriate test result cannot be obtained.

The present invention has been made in order to solve such related-art problems, and an object thereof is to provide an ultrasound diagnostic apparatus and a method of controlling an ultrasound diagnostic apparatus that perform a compression test at an appropriate position regardless of the skill of the user.

In order to achieve the above object, an ultrasound diagnostic apparatus according to an aspect of the present invention, which performs a compression test with respect to at least two points of a popliteal vein and a common femoral vein of a subject, comprises an ultrasound probe, an image acquisition unit that acquire an ultrasound image by transmitting an ultrasound beam toward the subject from the ultrasound probe, a vein detection unit that detects the popliteal vein included in the ultrasound image acquired by the image acquisition unit, and an operation guiding unit that guides a user, in a case where the compression test of the popliteal vein is performed, to operate the ultrasound probe such that the ultrasound probe is positioned at a position in which only one popliteal vein is included in the ultrasound image acquired by the image acquisition unit based on the number of the popliteal veins detected by the vein detection unit.

It is preferable that the operation guiding unit guide the user to operate the ultrasound probe to fix the position of the ultrasound probe in a case where only one popliteal vein is detected by the vein detection unit, and guide the user to move the ultrasound probe to an upper side of a back of a knee of the subject in a case where a plurality of the popliteal veins are detected by the vein detection unit.

It is preferable that the ultrasound diagnostic apparatus further comprise a probe movement range determining unit that determines whether a movement range of the ultrasound probe by the user from a point in time when the ultrasound probe is guided by the operation guiding unit to be moved to an upper side of a back of a knee of the subject is within a predetermined range, in which the operation guiding unit guides the user to move the ultrasound probe to the back of the knee of the subject in a case where the probe movement range determining unit determines that the movement range of the ultrasound probe is beyond the predetermined movement range.

In this case, the probe movement range determining unit may determine that the movement range of the ultrasound probe is beyond the predetermined movement range in a case where the number of frames of a plurality of the ultrasound images acquired by the image acquisition unit from a point in time when the operation of the ultrasound probe is guided by the operation guiding unit such that the ultrasound probe is moved to an upper side of the back of the knee exceeds a predetermined number of frames.

Alternatively, the probe movement range determining unit may determine that the movement range of the ultrasound probe is beyond the predetermined movement range in a case where an elapsed time from a point in time when the operation of the ultrasound probe is guided by the operation guiding unit such that the ultrasound probe is moved to an upper side of the back of the knee exceeds a predetermined time.

Also, the ultrasound probe may include an acceleration sensor, the ultrasound diagnostic apparatus may further comprise a probe movement distance estimating unit that estimates a movement distance of the ultrasound probe based on an acceleration of the ultrasound probe measured by the acceleration sensor, and the probe movement range determining unit may determine that the movement range of the ultrasound probe is beyond the predetermined movement range in a case where the movement distance of the ultrasound probe estimated by the probe movement distance estimating unit from a point in time when the operation of the ultrasound probe is guided by the operation guiding unit such that the ultrasound probe is moved to an upper side of the back of the knee exceeds a predetermined distance.

The ultrasound diagnostic apparatus may further comprise a display unit, in which the operation guiding unit causes the display unit to display operation guidance on the ultrasound probe for the user.

A method of controlling an ultrasound diagnostic apparatus that performs a compression test with respect to at least two points of a popliteal vein and a common femoral vein of a subject according to another aspect of the present invention comprises transmitting an ultrasound beam toward a back of a knee of the subject from an ultrasound probe to acquire an ultrasound image, detecting the popliteal vein included in the acquired ultrasound image, and guiding, in a case where the compression test of the popliteal vein is performed, a user to operate the ultrasound probe based on the number of the detected popliteal veins such that the ultrasound probe is positioned at a position in which only one popliteal vein is included in the acquired ultrasound image.

According to the present invention, an ultrasound diagnostic apparatus comprises a vein detection unit that detects the popliteal vein included in the ultrasound image acquired by the image acquisition unit, and an operation guiding unit that guides a user, in a case where the compression test of the popliteal vein is performed, to operate the ultrasound probe such that the ultrasound probe is positioned at a position in which only one popliteal vein is included in the ultrasound image acquired by the image acquisition unit based on the number of the popliteal veins detected by the vein detection unit, and thus it is possible to perform a compression test at an appropriate position regardless of the skill of the user.

DESCRIPTION OF THE PREFERRED EMBODIMENTS

Hereinafter, embodiments of the present invention will be described based on the accompanying drawings.

Embodiment 1

Figure 1:
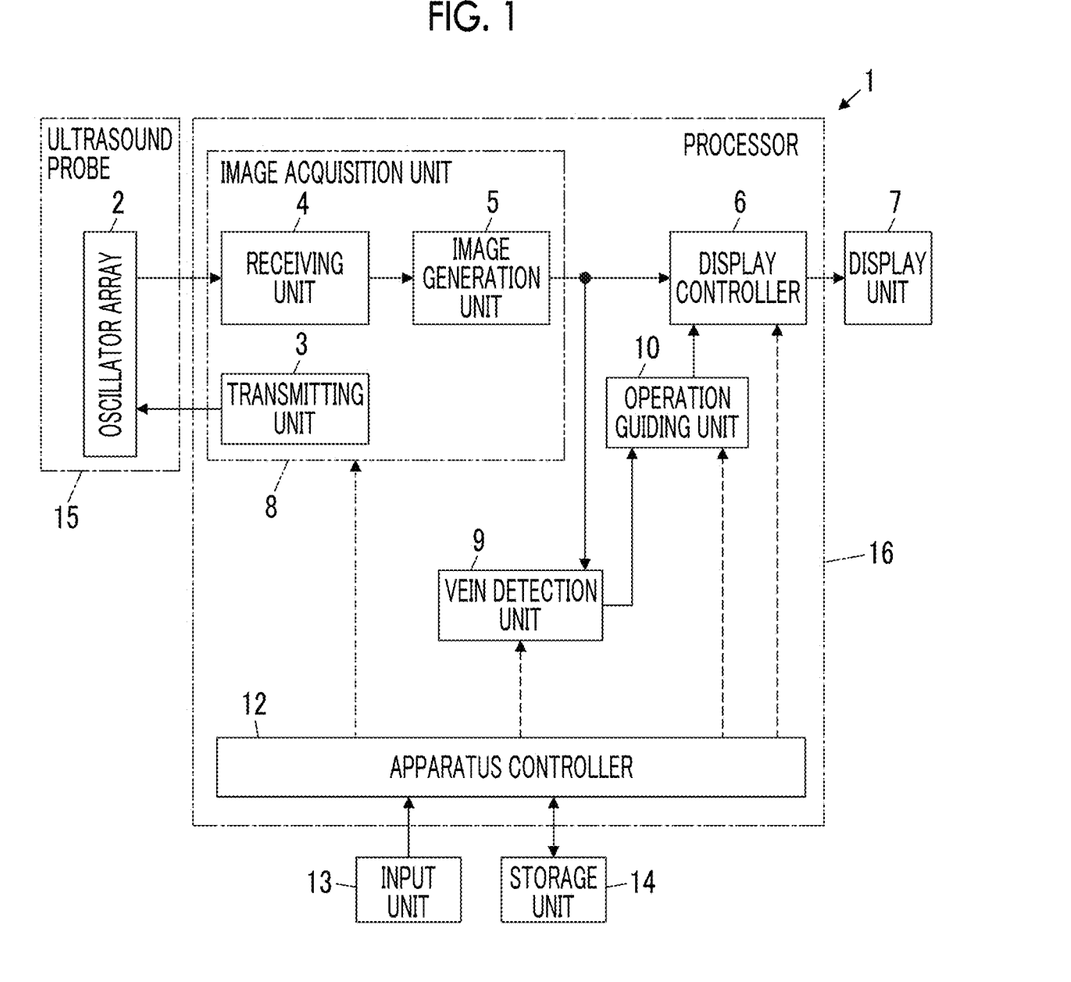
FIG. 1 is a block diagram showing a configuration of an ultrasound diagnostic apparatus according to Embodiment 1 of the present invention.

A configuration of an ultrasound diagnostic apparatus 1 according to Embodiment 1 of the present invention is shown in FIG. 1. As shown in FIG. 1, the ultrasound diagnostic apparatus 1 comprises an oscillator array 2, and a transmitting unit 3 and a receiving unit 4 are connected to the oscillator array 2. An image generation unit 5, a display controller 6, and a display unit 7 are sequentially connected to the receiving unit 4. An image acquisition unit 8 is configured by the transmitting unit 3, the receiving unit 4, and the image generation unit 5. A vein detection unit 9 is connected to the image generation unit 5, and an operation guiding unit 10 is connected to the vein detection unit 9. The operation guiding unit 10 is connected to the display controller 6.

The apparatus controller 12 is connected to the display controller 6, the image acquisition unit 8, the vein detection unit 9, the operation guiding unit 10, and the input unit 13 and the storage unit 14 are connected to the apparatus controller 12. The apparatus controller 12 and the storage unit 14 are connected to each other so as to be capable of transferring information bidirectionally.

The oscillator array 2 is included in the ultrasound probe 15, and a processor 16 is configured by the display controller 6, the image acquisition unit 8, the vein detection unit 9, the operation guiding unit 10, and the apparatus controller 12.

The oscillator array 2 of the ultrasound probe 15 shown in FIG. 1 has a plurality of oscillators arranged in one dimension or two dimensions. These oscillators transmit ultrasound waves in accordance with drive signals supplied from the transmitting unit 3, respectively, and receive ultrasound echoes from the subject to output the received signals. The respective oscillators are configured by, for example, forming electrodes to both ends of piezoelectric material made of a piezoelectric ceramic represented by lead zirconate titanate (PZT), a polymeric piezoelectric element represented by polyvinylidene difluoride (PVDF), and a piezoelectric single crystal represented by a lead magnesium niobate-lead titanate solid solution (PMN-PT).

The transmitting unit 3 of the image acquisition unit 8 includes, for example, a plurality of pulse generators, and adjusts the amounts of delay of the respective drive signals to supply the adjusted drive signals to the plurality of oscillators such that the ultrasound waves transmitted from the plurality of oscillators of the oscillator array 2 form an ultrasound beam, based on a transmission delay pattern selected in accordance with the control signals from the apparatus controller 12. In this way, in a case where a pulsed or consecutive wave-like voltage is applied to electrodes of the plurality of oscillators of the oscillator array 2, the piezoelectric material expands and contracts, a pulsed or consecutive wave-like ultrasound wave is generated from the respective oscillators, and the ultrasound beam is formed from a synthetic wave of the ultrasound waves.

The transmitted ultrasound beam is reflected in, for example, targets such as a part of the subject and is propagated toward the oscillator array 2 of the ultrasound probe 15. The ultrasound echoes propagated toward the oscillator array 2 in this way are received by the respective oscillators that constitute the oscillator array 2. In this case, the respective oscillators that constitute the oscillator array 2 expand and contract by receiving the propagated ultrasound echoes, to generate electrical signals, and output the electrical signals to the receiving unit 4.

Figure 2:
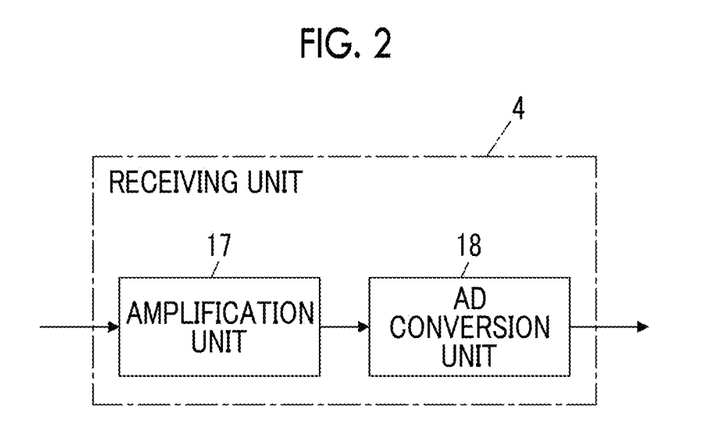
FIG. 2 is a block diagram showing an internal configuration of a receiving unit according to Embodiment 1 of the present invention.

The receiving unit 4 of the image acquisition unit 8 processes the received signals output from the oscillator array 2 in accordance with the control signals from the apparatus controller 12. As shown in FIG. 2, the receiving unit 4 has a configuration that an amplification unit 17 and an analog-digital (AD) conversion unit 18 are serially connected. The amplification unit 17 amplifies the received signals input from the respective oscillators that constitute the oscillator array 2, and transmits the amplified received signals to the AD conversion unit 18. The AD conversion unit 18 converts the received signals transmitted from the amplification unit 17 into digitalized data, and sends the data to the image generation unit 5 of the image acquisition unit 8.

Figure 3:
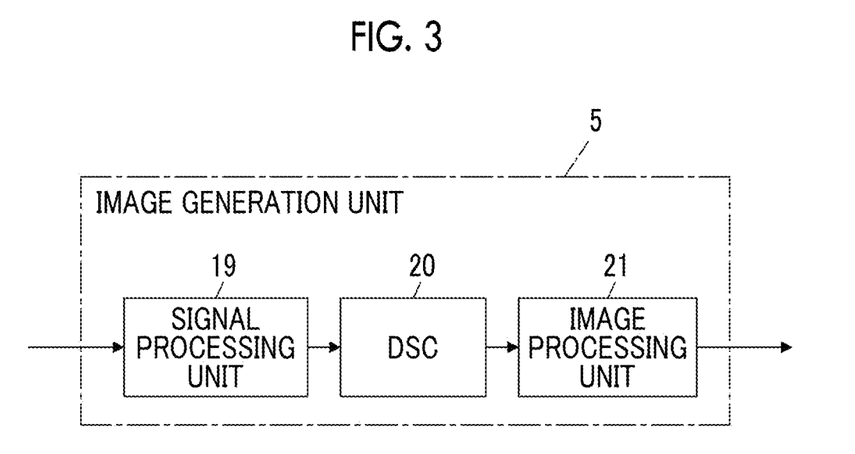
FIG. 3 is a block diagram showing an internal configuration of an image generation unit according to Embodiment 1 of the present invention.

As shown in FIG. 3, the image generation unit 5 of the image acquisition unit 8 has a configuration that a signal processing unit 19, a digital scan converter (DSC) 20, and an image processing unit 21 are serially connected. The signal processing unit 19 performs reception focus processing that addition (phasing addition) is performed by giving each delay to each data of the received signals, based on a reception delay pattern selected in accordance with the control signals from the apparatus controller 12. With the reception focus processing, sound ray signals in which focal points of the ultrasound echoes are narrowed to one scan line are generated. Additionally, the signal processing unit 19 subjects the generated sound ray signals to the correction of damping resulting from a propagation distance depending on the depth at a position where the ultrasound waves are reflected, and then performs envelope detection processing to generate B-mode image signals indicating a tissue in the subject. The B-mode image signals generated in this way are output to the DSC 20.

The DSC 20 of the image generation unit 5 raster-converts the B-mode image signals into image signals based on a scan mode of normal television signals to generate the ultrasound image. The image processing unit 21 of the image generation unit 5 subjects the image data obtained in the DSC 20 to various kinds of required image processing such as brightness correction, grayscale correction, sharpness correction, and color correction, and then outputs an ultrasound image to the display controller 6, and the vein detection unit 9.

The vein detection unit 9 of the processor 16 performs image analysis with respect to the ultrasound image acquired by the image acquisition unit 8, detects the popliteal vein, and calculates the number of the detected popliteal veins. In this case, the vein detection unit 9 detects the popliteal vein by, for example, recognizing the cross section of the popliteal vein included in the ultrasound image. The cross section of the popliteal vein represents the section of the popliteal vein in a case of cutting the popliteal vein across a central axis of the popliteal vein. More specifically, for example, the vein detection unit 9 can recognize the cross section of the popliteal vein by storing typical pattern data as a template in advance, calculating the similarity to the pattern data while searching the image with the template, and assuming the popliteal vein is present in the position where the similarity is equal to or larger than a threshold value and is maximum. The artery existing around the popliteal vein may be included in the ultrasound image, but the vein detection unit 9 can recognize the popliteal vein by pattern recognition using the template based on the typical positional relationship between the popliteal vein and the artery, a relative value of typical diameter of the popliteal vein with respect to the typical diameter of the artery. The vein detection unit 9 can recognize the popliteal vein by using a so-called Doppler signal as an auxiliary in addition to pattern recognition.

A machine learning method described in Csurka et al.: Visual Categorization with Bags of Keypoints, Proc. of ECCV Workshop on Statistical Learning in Computer Vision, pp. 59-74 (2004), a general image recognition method using deep learning described in Krizhevsky et al.: Image Net Classification with Deep Convolutional Neural Networks, Advances in Neural Information Processing Systems 25, and pp. 1106-1114 (2012), or the like can be used for the calculation of the similarity in addition to the simple template matching. Example of a general image recognition method using deep learning includes image classification by a convolutional neural network (CNN) in which an ultrasound image including a popliteal vein is positive and an ultrasound image not including a popliteal vein is negative, a semantic segmentation of vein region and artery region using a neural network comprising an up-sampling layer such as U-Net, and vein detection using a bounding box detection model such as Mask-R-CNN.

In general, the DVT that is a disease in which a thrombus occurs in a deep vein is known, and the DVT often occurs in a lower thigh. Although a normal deep vein in which the thrombus does not occur is easily deformed by compression, the deep vein in which the thrombus occurs is not easily deformed due to the compression. Therefore, as a test for the DVT, for example, a so-called compression test for observing a cross section of the compressed deep vein while compressing the deep vein having a concern that the DVT may occur is performed. As a method of quickly detecting DVT generated in the lower thigh of the subject, a so-called two-point compression method is known in which a compression test is performed with respect to at least only two points of the popliteal vein and the common femoral vein. The popliteal vein is generally observed as one blood vessel in a case where the ultrasound probe is brought into contact with the back of the knee of the subject, but in some cases, the vein branches to an upper side of the back of the knee depending on the subject, and a plurality of small blood vessels are observed in a case where the ultrasound probe is brought into contact with the back of the knee of the subject. In general, the larger thrombus is likely to occur as the vein is thicker, and in a case where the thrombus is peeled off from the inner wall of the vein and flows to the central side of the vein, pulmonary embolism is likely to be caused, and thus it is desirable that the compression test is performed above the branched part of the vein, that is, at a position in which only one popliteal vein is observed.

In a case where the compression test of the popliteal vein is performed, the operation guiding unit 10 of the processor 16 guides the user to operate the ultrasound probe 15 depending on the number of popliteal veins detected by the vein detection unit 9 such that the ultrasound probe 15 is positioned at the position in which only one popliteal vein is included in the ultrasound image acquired by the image generation unit 5. For example, in a case where the ultrasound probe 15 is positioned at the back of the knee of the subject by the user and only one popliteal vein is detected by the vein detection unit 9, the operation guiding unit 10 guides the user to fix the position of the ultrasound probe 15, and in a case where two popliteal veins are detected by the vein detection unit 9, guides the user to move the ultrasound probe 15 to an upper side of the back of the knee of the subject. Thus, in a case where the popliteal vein branches to an upper side of the back of the knee, it prevents the user from performing the compression test on the back of the knee.

In this case, the operation guiding unit 10 can guide the user to operate the ultrasound probe 15 by, for example, displaying the text and the image indicating the guidance for the user on the display unit 7. Additionally, although not shown, for example, a voice generation unit that generates voice can also be provided in the ultrasound diagnostic apparatus 1, and the operation guiding unit 10 can also guide the user by the voice via the voice generation unit.

The apparatus controller 12 of the processor 16 performs control of the respective units of the ultrasound diagnostic apparatus 1 based on the programs that are stored in advance in the storage unit 14 and the like and the operation of the user via the input unit 13.

Under the control of the apparatus controller 12, the display controller 6 of the processor 16 performs predetermined processing on an ultrasound image generated by the image generation unit 5 of the image acquisition unit 8, and displays the ultrasound image on the display unit 7.

The display unit 7 of the ultrasound diagnostic apparatus 1 displays the ultrasound image under the control of the display controller 6, and includes display devices such as a liquid crystal display (LCD), and an organic electroluminescence (EL) display.

The input unit 13 of the ultrasound diagnostic apparatus 1 is a device for the user to perform input operation, and can be configured to comprise a keyboard, a mouse, a trackball, a touchpad, a touch panel, and the like.

The storage unit 14 stores operating programs and the like of the ultrasound diagnostic apparatus 1, and as the storage unit 14, a recording medium such as a hard disc drive (HDD), a solid state drive (SSD), a flexible disc (ED), a magneto-optical (MO) disc, a magnetic tape (MT), a random access memory (RAM), a compact disc (CD), a digital versatile disc (DVD), a secure digital (SD) card, a universal serial bus (USB) memory, or the like, or a server can be used.

In addition, the processor 16 having the display controller 6, the image acquisition unit 8, the vein detection unit 9, the operation guiding unit 10, and the apparatus controller 12 is configured from a central processing unit (CPU) and control programs for making the CPU perform various kinds of processing. However, the processor 16 may be configured from a field programmable gate array (FPGA), a digital signal processor (DSP), an application specific integrated circuit (ASIC), or other integrated circuits (ICs), or may be configured by combining them.

Also, the display controller 6, the image acquisition unit 8, the vein detection unit 9, the operation guiding unit 10, and the apparatus controller 12 of the processor 16 can be partially or wholly integrated into one CPU.

Figure 4:
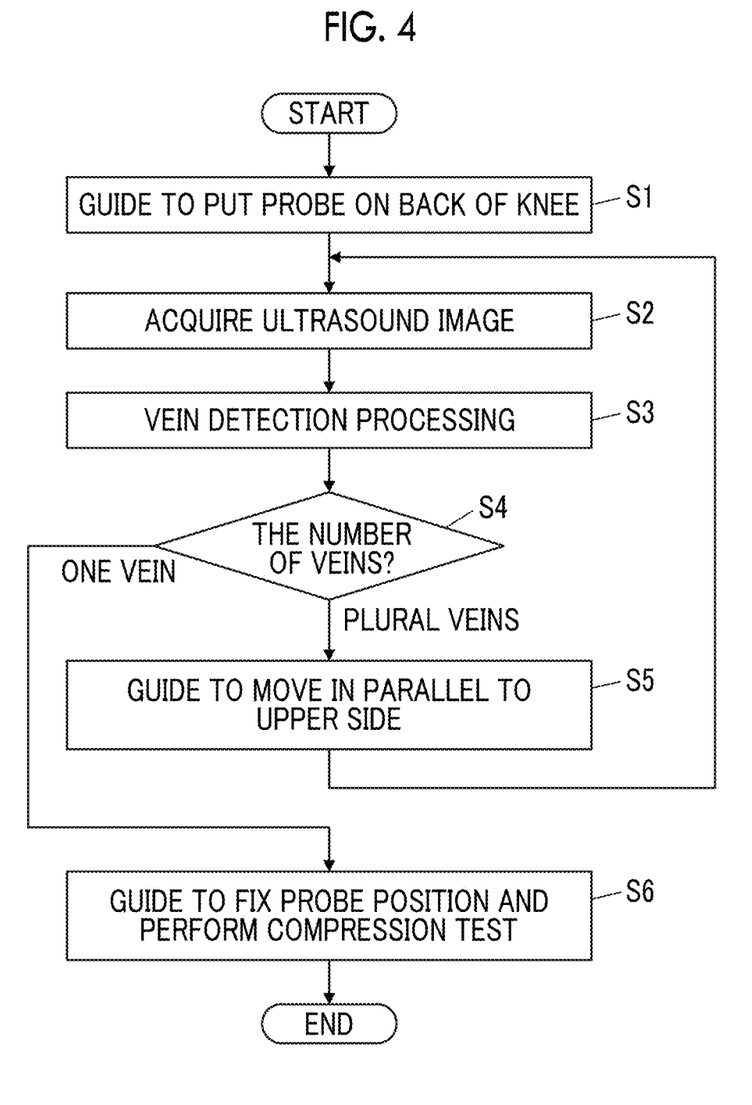
FIG. 4 is a flowchart showing an operation of the ultrasound diagnostic apparatus according to Embodiment 1 of the present invention.

Next, the operation of the ultrasound diagnostic apparatus 1 in Embodiment 1 will be described in detail using a flowchart shown in FIG. 4. The flowchart shown in FIG. 4 shows the operation of the ultrasound diagnostic apparatus 1 in a case where the compression test is performed with respect to the popliteal vein of the subject.

First, in step S1, the operation guiding unit 10 guides the user to position the ultrasound probe 15 on the back of the knee of the subject. Although not shown, in this case, the operation guiding unit 10 can display, for example, text indicating that the ultrasound probe 15 is positioned at the back of the knee of the subject on the display unit 7. In this way, in a case where the operation guiding unit 10 provides the guidance to the user, the user operates the ultrasound probe 15 to position the ultrasound probe on the back of the knee of the subject.

Next, in step S2, the ultrasound beam is transmitted toward the back of the knee of the subject from the oscillator array 2 of the ultrasound probe 15, and the received signals are generated by the oscillator array 2 based on ultrasound echoes propagated toward the oscillator array 2 from the back of the knee of the subject. As the received signals generated in this way are sequentially processed by the receiving unit 4 and the image generation unit 5 of the image acquisition unit 8, the ultrasound image representing the cross section of the back of the knee of the subject is acquired.

In step S3, the vein detection unit 9 detects the popliteal vein included in the ultrasound image by performing image processing with respect to the ultrasound image acquired in step S2 and calculates the number of the detected popliteal veins. In this case, for example, the vein detection unit 9 can detect the vein by recognizing the cross section of the blood vessel included in the ultrasound image, and determining whether the recognized blood vessel is the vein or the artery based on the diameter of the recognized blood vessel, the thickness of the vascular wall, and the circularity of the cross section of the blood vessel.

In following step S4, the operation guiding unit 10 determines that the number of the popliteal veins detected in step S3 is one or plural by receiving the information indicating the number of popliteal veins detected in step S3 from the vein detection unit 9. Based on the determination on whether the popliteal vein detected in step S3 is one or plural, the operation guiding unit 10 guides the user to operate the ultrasound probe 15 such that only one popliteal vein is included in the ultrasound image acquired in step S2 and the ultrasound probe 15 is positioned at the position in which the compression test of the popliteal vein is performed.

Figure 5:
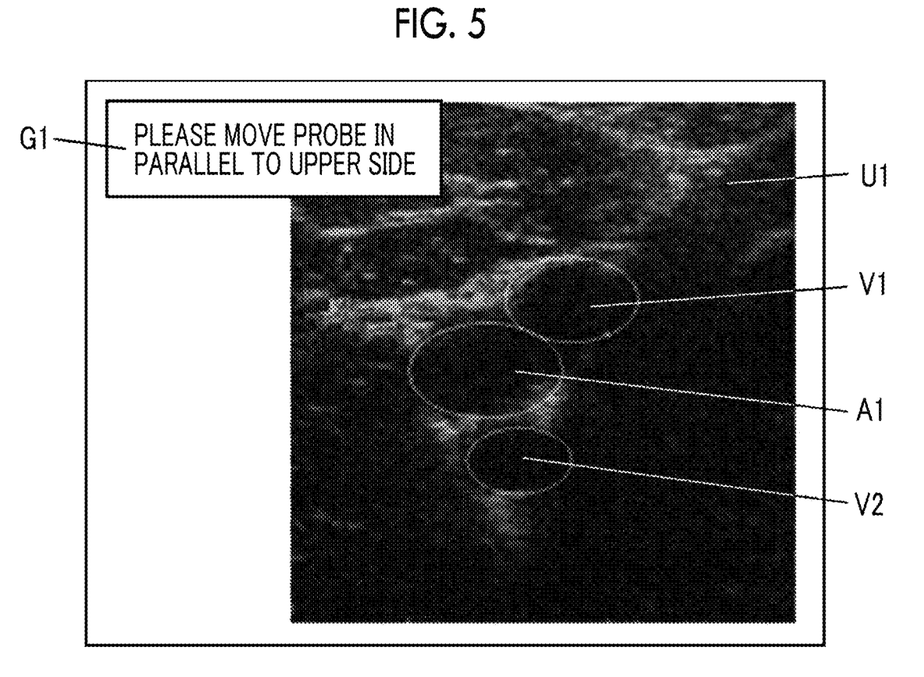
FIG. 5 is a diagram showing an example of operation guidance in Embodiment 1 of the present invention.

In step S4, in a case where the determination is made that the number of popliteal veins detected in step S3 is plural, the process proceeds to step S5. In step S5, the operation guiding unit 10 guides the user to move the ultrasound probe 15 in parallel to an upper side of the back of the knee of the subject. In this case, as shown in FIG. 5, the operation guiding unit 10 can guide the user to operate the ultrasound probe 15 by, for example, displaying a guide panel G1 including the text indicating the guidance for the user on the display unit 7. In the example of FIG. 5, the guide panel G1 including the text "please move probe in parallel upward" is displayed while being superimposed on an ultrasound image U1 including two of popliteal vein V1 and popliteal vein V2, and one artery A1. In this way, in a case where the operation of the ultrasound probe 15 is guided to the user, the user moves the ultrasound probe 15 in parallel to an upper side of the back of the knee of the subject. Thus, in a case where the popliteal vein branches to an upper side of the back of the knee, it prevents the user from performing the compression test on the back of the knee.

In this way, in a state where the ultrasound probe 15 is moved by the user in parallel to an upper side of the back of the knee, the process returns to step S2, and the image acquisition unit 8 acquires a new ultrasound image.

In step S3, the vein detection unit 9 detects the popliteal vein included in the ultrasound image newly acquired in step S2 and calculates the number of the detected popliteal veins.

In following step S4, the operation guiding unit 10 determines whether the number of popliteal veins detected in step S3 is only one or plural, and provides different guidance to the user depending on the determination on whether the number of popliteal veins is only one or plural.

In a case where the determination is made that the number of popliteal veins is plural in step S4, the process proceeds to step S5, and the operation guiding unit 10 provides the guidance for moving the ultrasound probe 15 in parallel to an upper side of the back of the knee. In this way, the processing items of step S2 to step S5 are repeated until the determination is made that the number of popliteal veins is only one in step S4.

Figure 6:
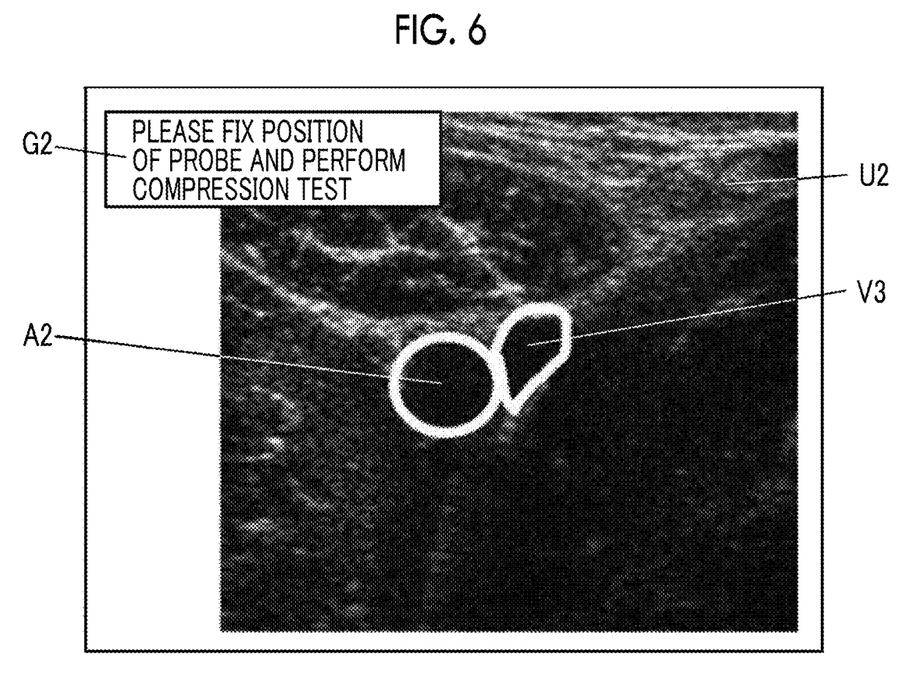
FIG. 6 is a diagram showing another example of operation guidance in Embodiment 1 of the present invention.

In a case where the determination is made that the number of popliteal veins is one in step S4, the process proceeds to step S6. In step S6, the operation guiding unit 10 guides the user to fix the ultrasound probe 15 at the position and perform the compression test. In this case, as shown in FIG. 6, the operation guiding unit 10 can guide the user to operate the ultrasound probe 15 by, for example, displaying a guide panel G2 including the text indicating the guidance for the user on the display unit 7. In the example of FIG. 6, the guide panel G2 including the text "please fix position of probe and perform compression test" is displayed while being superimposed on an ultrasound image U2 including only one cross section of the popliteal vein V3 and only one cross section of the artery A2. In this way, in a case where the operation of the ultrasound probe 15 is guided to the user, the user fixes the position of the ultrasound probe 15 and performs the compression test. As a result, the operation of the ultrasound diagnostic apparatus 1 in a case where the compression test is performed with respect to the popliteal vein of the subject ends.

As described above, in the ultrasound diagnostic apparatus 1 according to Embodiment 1, in a case where the popliteal vein included in the ultrasound image is detected, in particular, a plurality of popliteal veins are detected, the operation of the ultrasound probe 15 is guided for the user such that the ultrasound probe 15 is positioned at an appropriate position regarding the compression test of the popliteal vein, and thus it is possible to perform the compression test at an appropriate position regardless of the skill of the user.

In Embodiment 1, the transmitting unit 3 and the receiving unit 4 of the image acquisition unit 8 is included in the processor 16, but the transmitting unit and the receiving unit can also be included in the ultrasound probe 15 instead of being included in the processor 16.

Also, in Embodiment 1, the vein detection unit 9 detects the popliteal vein by using a method such as pattern recognition in a case of detecting the popliteal vein included in the ultrasound image, but the detection accuracy of the popliteal vein can be improved by using a method of discriminating between the artery and the vein as an auxiliary.

For example, the vein detection unit 9 can discriminate between the vein and the artery by performing the image analysis on the ultrasound image. In general, the vascular wall of the vein is thinner than the vascular wall of the artery, the internal pressure of the vein is lower than the internal pressure of the artery, and the circularity of the cross section of the vein is lower than the circularity of the cross section of the artery, and thus the vein detection unit 9 can discriminate between the vein and the artery based on, for example, the diameter of the cross section of the blood vessel, the thickness of the vascular wall, and the circularity of the cross section of the blood vessel included in the ultrasound image. For example, the vein detection unit 9 can recognize the vein and the artery included in the ultrasound image by reflecting a difference between the diameters of the cross sections of the vein and the artery, a difference between the thicknesses of the vascular walls, and a difference between the circularities of the cross sections on the template or the feature amount vector in the machine learning method. For example, the vein detection unit 9 can classify the vein and the artery, by deep learning such as U-Net, by using the difference between the diameters of the cross sections of vein and the artery, the difference between the thicknesses of the vascular walls, and the circularities between the cross sections.

The artery beats in response to the heart beat, but the vein does not beat, and thus, for example, the vein detection unit 9 can discriminate between the vein and the artery by determining whether the blood vessel included in the ultrasound image beats. More specifically, for example, the vein detection unit 9 can calculate the diameter of the blood vessel included in the ultrasound image with respect to the ultrasound images sequentially acquired by the image acquisition unit 8 in a state where the position of the ultrasound probe 15 is fixed, and determine that the blood vessel having periodically changed diameter is the artery, and the blood vessel having not periodically changed diameter is the vein.

In addition, the vein and the artery can be discriminated by acquiring the movement of the vascular wall accompanying the beating by a so-called Doppler signal. More specifically, for example, although not shown, a Doppler processing unit that generates a so-called Doppler signal by analyzing the frequency of the data generated by the receiving unit 4 can be provided in the ultrasound diagnostic apparatus 1, and the vein detection unit 9 can determine that the blood vessel in which the signal intensity of the Doppler signal obtained by the Doppler processing unit changes periodically is the artery, and the blood vessel in which the signal intensity of the Doppler signal changes less is the vein.

For example, the vein detection unit 9 can discriminate between the vein and the artery by optionally combining a plurality of discriminating methods. The vein detection unit 9 can detect the popliteal vein by learning a plurality of discriminating methods by a general image recognition method such as deep learning. More specifically, the vein detection unit 9 can classify or detect the vein and the artery by deep learning by using the Doppler image based on the Doppler signal. The vein detection unit 9 can determine the vein and the artery by using the ultrasound image of a plurality of frames by calculating the change rates of the diameter and the area of the blood vessel for each region classified as the blood vessel.

In Embodiment 1, the processing items of step S2 to step S5 are repeated until the determination is made that the number of popliteal veins included in the ultrasound image is only one in step S4. In this case, for example, instead of the vein detection processing items of step S3, by tracking the position of the popliteal vein in the ultrasound images sequentially acquired by the image acquisition unit 8 and detecting a bifurcation point in which a plurality of popliteal veins merge into one popliteal vein, the information indicating whether the number of popliteal veins included in the ultrasound image is only one can be obtained. For example, in order to perform such processing, although not shown, the ultrasound diagnostic apparatus 1 can be provided with a bifurcation point detection unit that tracks the position of the popliteal vein included in the ultrasound image by performing the pattern matching between adjacent frames with respect to the ultrasound images sequentially acquired by the image acquisition unit 8 and detects the bifurcation point in which a plurality of popliteal veins merge into one popliteal vein. Accordingly, it is not necessary to perform the vein detection processing every time a new ultrasound image is acquired, and thus the calculation load of the ultrasound diagnostic apparatus 1 can be reduced.

In a case where the discrimination is made that a plurality of popliteal veins are included in the ultrasound image in step S4, for example, although not shown, the ultrasound diagnostic apparatus 1 can be provided with a three-dimensional data generating unit that generates three-dimensional data representing a three-dimensional structure of the popliteal vein based on the result of the vein detection processing performed on the ultrasound images sequentially acquired by the image acquisition unit 8. In this case, the operation guiding unit 10 can guide the user to position the ultrasound probe 15 at an appropriate position for the compression test of the popliteal vein based on the three-dimensional data generated by the three-dimensional data generating unit.

In the DVT test using the two-point compression method, the compression test on the common femoral vein is performed in addition to the compression test on the popliteal vein of the subject, and thus, for example, the operation guiding unit 10 can guide the user to position the ultrasound probe 15 on the back of the knee and in the inguinal region of the subject. In this case, for example, although not shown, the ultrasound diagnostic apparatus 1 can be provided with a probe position determination unit that recognizes the part of the subject included in the ultrasound image acquired by the image acquisition unit 8 and discriminates whether the ultrasound probe 15 is positioned at the back of the knee or the inguinal region, and the operation guiding unit 10 can guide the user to position the ultrasound probe 15 on the back of the knee and the inguinal region based on the determination result by the probe position determination unit.

In general, the hardness of the back of the knee and the hardness of the inguinal region are different, for example, the ultrasound diagnostic apparatus 1 can be provided with a hardness detection unit that generates a so-called elastography image and detects the hardness of the part included in the ultrasound image from the generated elastography image, and the probe position determination unit can determine whether the ultrasound probe 15 is positioned at the back of the knee or in the inguinal region based on the hardness of the part detected by the hardness detection unit.

Embodiment 2

In Embodiment 1, in a case where a plurality of popliteal veins are detected by the vein detection unit 9, until only one popliteal vein is detected, the ultrasound image is acquired while moving the ultrasound probe 15 to an upper side of the back of the knee, but the movement range of the ultrasound probe 15 can be determined such that the ultrasound probe 15 does not move too much upward.

Figure 7:
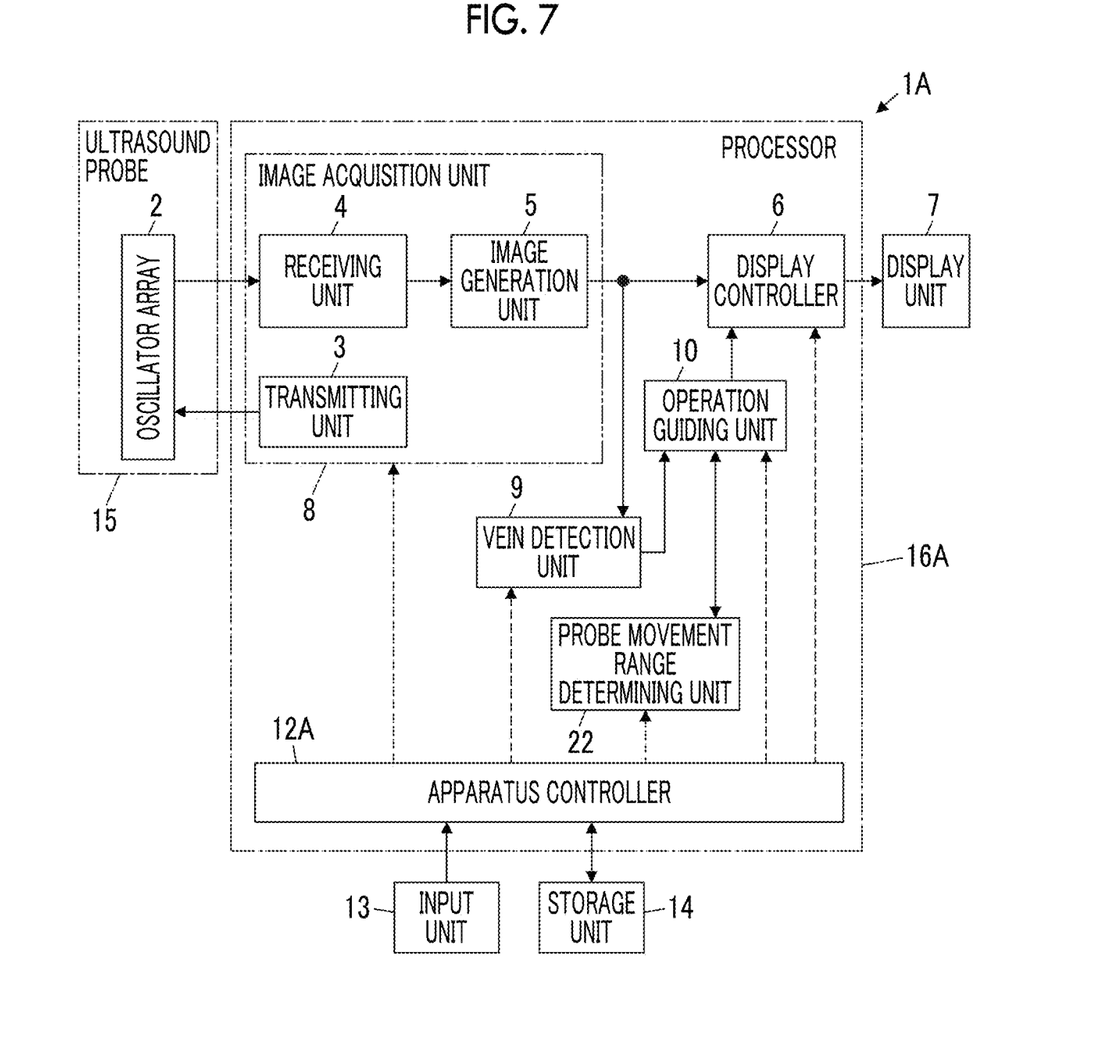
FIG. 7 is a block diagram showing a configuration of an ultrasound diagnostic apparatus according to Embodiment 2 of the present invention.

The configuration of an ultrasound diagnostic apparatus 1A according to Embodiment 2 is shown in FIG. 7. The ultrasound diagnostic apparatus 1A of Embodiment 2 comprises an apparatus controller 12A instead of the apparatus controller 12 in the ultrasound diagnostic apparatus 1 of Embodiment 1 shown in FIG. 1, and further comprises a probe movement range determining unit 22.

In the ultrasound diagnostic apparatus 1A according to Embodiment 2, the probe movement range determining unit 22 is connected to the operation guiding unit 10. The apparatus controller 12A is connected to the display controller 6, the image acquisition unit 8, the vein detection unit 9, the operation guiding unit 10, and the input unit 13, the storage unit 14, and the probe movement range determining unit 22. A processor 16A is configured by the display controller 6, the image acquisition unit 8, the vein detection unit 9, the operation guiding unit 10, the probe movement range determining unit 22, and the apparatus controller 12A.

The probe movement range determining unit 22 of the processor 16A determines whether the movement range of the ultrasound probe 15 by the user from a point in time when the vein detection unit 9 detects a plurality of popliteal veins and the operation guiding unit 10 provides the guidance for moving the ultrasound probe 15 to an upper side of the back of the knee of the subject is within a predetermined range. For example, the probe movement range determining unit 22 can determine that the movement range of the ultrasound probe 15 is beyond the predetermined range in a case where the ultrasound images more than a predetermined number of frames are acquired by the image acquisition unit 8 or in a case where a predetermined time has elapsed, from a point in time when the operation guiding unit 10 provides the guidance for moving the ultrasound probe 15 to an upper side of the back of the knee.

The predetermined number of frames representing a predetermined movement range of the ultrasound probe 15 and a predetermined time can be stored in the probe movement range determining unit 22 and the storage unit 14 in advance.

Figure 8:
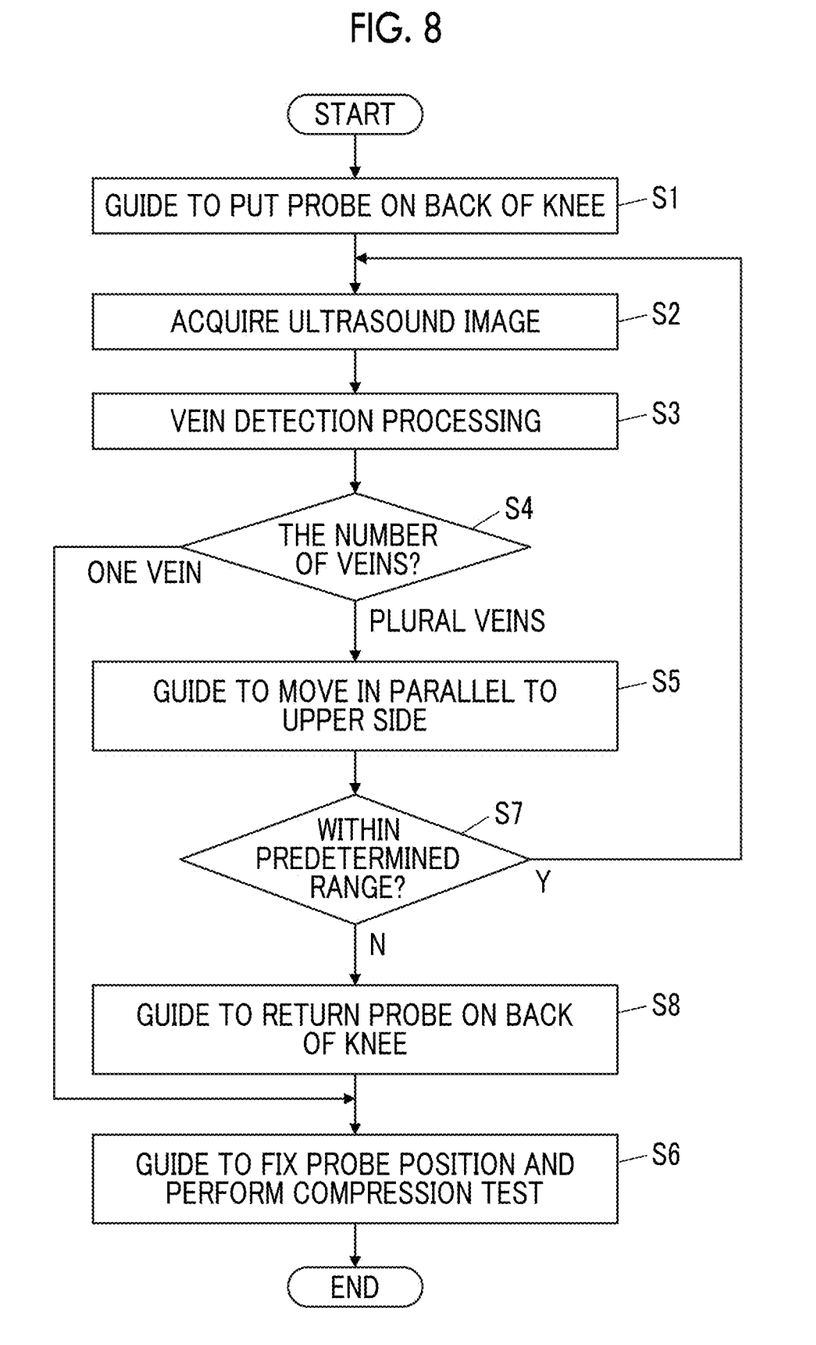
FIG. 8 is a flowchart showing an operation of the ultrasound diagnostic apparatus according to Embodiment 2 of the present invention.

Next, the operation of the ultrasound diagnostic apparatus 1A according to Embodiment 2 will be described using the flowchart shown in FIG. 8. The flowchart shows an operation of the ultrasound diagnostic apparatus 1A in a case of performing the compression test on the back of the knee, and step S7 and step S8 are added to the flowchart of Embodiment 1 shown in FIG. 4.

First, in step S1, the operation guiding unit 10 guides the user to position the ultrasound probe 15 on the back of the knee of the subject. In this case, as shown in FIG. 5, the operation guiding unit 10 can display the guide panel G1 including the text indicating the guidance for the user on the display unit 7. The user positions the ultrasound probe 15 on the back of the knee of the subject in accordance with the guidance from the operation guiding unit 10.

In step S2, in a case where the image acquisition unit 8 acquires the ultrasound image, the process proceeds to step S3, the vein detection unit 9 detects the popliteal vein included in the acquired ultrasound image and calculates the number of the detected popliteal veins.

In following step S4, the operation guiding unit 10 determines whether the number of the popliteal veins detected in step S3 is only one or plural. In a case where the determination is made that the number of popliteal veins is plural in step S4, the process proceeds to step S5, and the operation guiding unit 10 provides the guidance for moving the ultrasound probe 15 in parallel to an upper side of the back of the knee. As a result, the user moves the ultrasound probe 15 in parallel to an upper side of the back of the knee.

In a case where the guidance is provided such that the ultrasound probe 15 is moved in parallel to an upper side of the back of the knee in step S5, and in step S7, the probe movement range determining unit 22 determines whether the movement range of the ultrasound probe 15 moved by the user is within a predetermined range. In this case, the probe movement range determining unit 22 can determine that the movement range of the ultrasound probe 15 is beyond the predetermined range in a case where the ultrasound images more than a predetermined number of frames are acquired by the image acquisition unit 8 or in a case where a predetermined time has elapsed, from a point in time when the operation guiding unit 10 provides the guidance for moving the ultrasound probe 15 to an upper side of the back of the knee.

In a case where the determination is made that the movement range of the ultrasound probe 15 is within a predetermined range in step S7, the process returns to step S2. In step S2, the image acquisition unit 8 newly acquires the ultrasound image, and in step S3, the popliteal vein included in the newly acquired ultrasound image is detected. In following step S4, determination is made whether the number of the popliteal veins detected in step S3 is only one or plural. In a case where the determination is made that the number of the detected popliteal veins is plural in step S4, the process proceeds to step S5, and the operation guiding unit 10 provides the guidance for moving the ultrasound probe 15 in parallel to an upper side of the back of the knee.

In step S7, the probe movement range determining unit 22 determines whether the movement range of the ultrasound probe 15 moved by the user is within a predetermined range.

In a case where the determination is made that the movement range of the ultrasound probe 15 is within a predetermined range in step S7, the process returns to step S2. As described above, the processing items of step S2 to step S5, and step S7 are repeated in a state where the determination is made that the number of the detected popliteal veins is plural in step S4 and until the determination is made that the movement range of the ultrasound probe 15 is beyond a predetermined range in step S7.

In a case where by repeating processing items of step S2 to step S5, and step S7, the ultrasound probe 15 is moved in parallel by the user to an upper side of the back of the knee of the subject, and thus the determination is made that the movement range of the ultrasound probe 15 is beyond a predetermined range in step S7, the process proceeds to step S8. In step SR, the operation guiding unit 10 guides the user to return the position of the ultrasound probe 15 to the back of the knee. As a result, the user positions the ultrasound probe 15 on the back of the knee.

In a case where the processing items of step S8 is completed, the process proceeds to step S6, and the operation guiding unit 10 guides the user to fix the position of the ultrasound probe 15 to the position and perform the compression test of the popliteal vein. In this case, as shown in FIG. 6, the operation guiding unit 10 can display the guide panel G2 including the text indicating the guidance for the user on the display unit 7. As a result, the operation of the ultrasound diagnostic apparatus 1A ends.

In a case where the determination is made that the number of the detected popliteal veins is only one in step S4, the process proceeds to step S6, the operation guiding unit 10 guides the user to fix the position of the ultrasound probe 15 to the position and perform the compression test of the popliteal vein, and then the operation of the ultrasound diagnostic apparatus 1A ends.

As described above, in the ultrasound diagnostic apparatus 1A according to Embodiment 2, in a case where the probe movement range determining unit 22 determines that the movement range of the ultrasound probe 15 is within a predetermined range, the operation guiding unit 10 provides the guidance for moving the ultrasound probe 15 in parallel to an upper side of the back of the knee, and in a case where the probe movement range determining unit 22 determines that the movement range of the ultrasound probe 15 is beyond a predetermined range, the operation guiding unit 10 provides the guidance for positioning the ultrasound probe 15 on the back of the knee, and thus in a case where a plurality of popliteal veins are detected by the vein detection unit 9 and the user moves the ultrasound probe 15 to an upper side of the back of the knee, it is possible to prevent the ultrasound probe 15 from moving to the position that is not suitable for performing the compression test of the popliteal vein.

In Embodiment 2, the probe movement range determining unit 22 determines that the movement distance of the ultrasound probe 15 is beyond the predetermined range in a case where the ultrasound images more than a predetermined number of frames is acquired by the image acquisition unit 8 or in a case where a predetermined time has elapsed, from a point in time when the operation guiding unit 10 provides the guidance for moving the ultrasound probe 15 in parallel to an upper side of the back of the knee of the subject, but the determination by the probe movement range determining unit 22 is not limited thereto.

Figure 9:
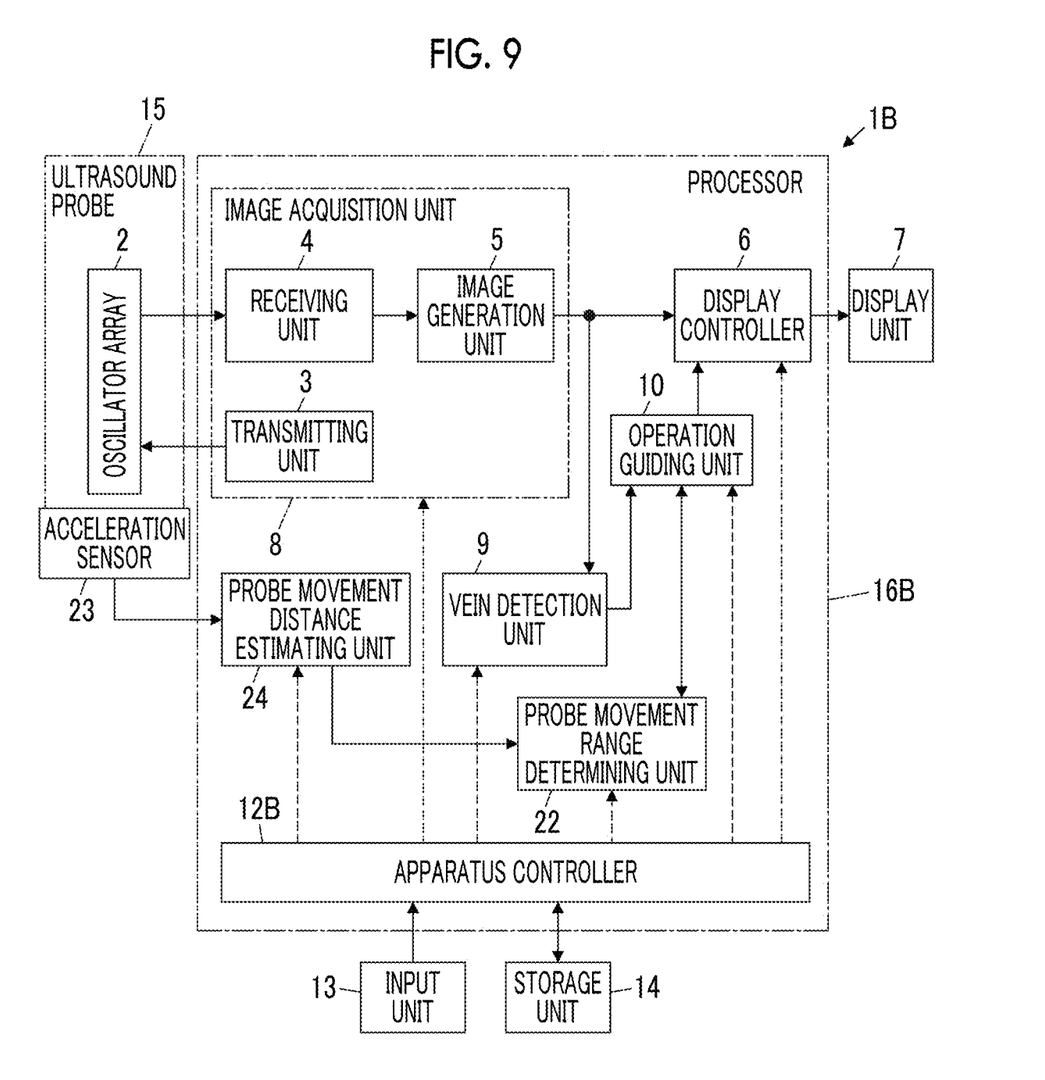
FIG. 9 is a block diagram showing a configuration of an ultrasound diagnostic apparatus according to a modification example of Embodiment 2 of the present invention.

For example, the probe movement range determining unit 22 can determine whether the movement range of the ultrasound probe 15 is within a predetermined range based on the movement distance of the ultrasound probe 15 estimated directly. The configuration of an ultrasound diagnostic apparatus 1B according to a modification example of Embodiment 2 is shown in FIG. 9. The ultrasound diagnostic apparatus 1B comprises an apparatus controller 12B instead of the apparatus controller 12A in the ultrasound diagnostic apparatus 1A of Embodiment 2 shown in FIG. 7, and further comprises an acceleration sensor 23 and a probe movement distance estimating unit 24.

In the ultrasound diagnostic apparatus 1B, the acceleration sensor 23 is attached to the ultrasound probe 15, and the probe movement distance estimating unit 24 is connected to the acceleration sensor 23. The probe movement range determining unit 22 is connected to the probe movement distance estimating unit 24. The apparatus controller 12B is connected to the display controller 6, the image acquisition unit 8, the vein detection unit 9, the operation guiding unit 10, the input unit 13, the storage unit 14, the probe movement range determining unit 22, and the probe movement distance estimating unit 24. A processor 16B is configured by the display controller 6, the image acquisition unit 8, the vein detection unit 9, the operation guiding unit 10, the apparatus controller 12B, the probe movement range determining unit 22, and the probe movement distance estimating unit 24.

The acceleration sensor 23 attached to the ultrasound probe 15 detects the acceleration of the ultrasound probe 15 moved by the user.

The probe movement distance estimating unit 24 of the processor 16B estimates the movement distance of the ultrasound probe 15 based on the acceleration of the ultrasound probe 15 detected by the acceleration sensor 23.

The probe movement range determining unit 22 determines whether the movement distance of the ultrasound probe 15 from a point in time when the operation guiding unit 10 provides the guidance for moving the ultrasound probe 15 in parallel to an upper side of the back of the knee is within a predetermined distance, based on the movement distance of the ultrasound probe 15 estimated by the probe movement distance estimating unit 24. As a result, the probe movement range determining unit 22 can accurately determine whether the movement range of the ultrasound probe 15 is within a predetermined range.

From the above description, the ultrasound diagnostic apparatus according to the following supplementary notes 1 to 7 can be grasped.

Supplementary Note 1

An ultrasound diagnostic apparatus that performs a compression test with respect to at least two points of a popliteal vein and a common femoral vein of a subject, the apparatus comprising an ultrasound probe, and a processor, wherein the processor is configured to acquire an ultrasound image by transmitting an ultrasound beam toward the subject from the ultrasound probe, detect the popliteal vein included in the acquired ultrasound image, and in a case where the compression test of the popliteal vein is performed, guide a user to operate the ultrasound probe such that the ultrasound probe is positioned at a position in which only one popliteal vein is included in the acquired ultrasound image based on the number of the detected popliteal veins.

Supplementary Note 2

The ultrasound diagnostic apparatus according to supplementary note 1, wherein the processor is further configured to guide the user to operate the ultrasound probe to fix the position of the ultrasound probe in a case where only one popliteal vein is detected, and guide the user to move the ultrasound probe to an upper side of a back of a knee of the subject in a case where a plurality of popliteal veins are detected.

Supplementary Note 3

The ultrasound diagnostic apparatus according to supplementary note 1 or 2, wherein the processor is further configure to determine whether a movement range of the ultrasound probe by the user from a point in time when the ultrasound probe is guided to be moved to an upper side of a back of a knee of the subject is within a predetermined range, and guide the user to move the ultrasound probe to the back of the knee of the subject in a case where the determination is made that the movement range of the ultrasound probe is beyond the predetermined movement range.

Supplementary Note 4

The ultrasound diagnostic apparatus according to supplementary note 3, wherein the processor is further configured to determine that the movement range of the ultrasound probe is beyond the predetermined movement range in a case where the number of frames of a plurality of the acquired ultrasound images exceeds a predetermined number of frames from a point in time when the operation of the ultrasound probe is guided such that the ultrasound probe is moved to an upper side of the back of the knee.

Supplementary Note 5

The ultrasound diagnostic apparatus according to supplementary note 3, wherein the processor is further configured to determine that the movement range of the ultrasound probe is beyond the predetermined movement range in a case where an elapsed time from a point in time when the operation of the ultrasound probe is guided such that the ultrasound probe is moved to an upper side of the back of the knee exceeds a predetermined time.

Supplementary Note 6

The ultrasound diagnostic apparatus according to supplementary note 3, wherein the ultrasound probe includes an acceleration sensor, the processor is further configured to estimate a movement distance of the ultrasound probe based on an acceleration of the ultrasound probe measured by the acceleration sensor, and determine that the movement range of the ultrasound probe from a point in time when the operation of the ultrasound probe is guided such that the ultrasound probe is moved to an upper side of the back of the knee is beyond the predetermined movement range in a case where the estimated movement distance of the ultrasound probe exceeds a predetermined distance.

Supplementary Note 7

The ultrasound diagnostic apparatus according to any one of supplementary notes 1 to 6, further comprising a display device, wherein the processor is further configured to cause the display device to display operation guidance on the ultrasound probe for the user.

EXPLANATION OF REFERENCES

1, 1A, 1B: ultrasound diagnostic apparatus
2: oscillator array
3: transmitting unit
4: receiving unit
5: image generation unit
6: display controller
7: display unit
8: image acquisition unit
9: vein detection unit
10: operation guiding unit
12, 12A, 12B: apparatus controller
13: input unit
14: storage unit
15: ultrasound probe
16, 16A, 16B: processor
17: amplification unit
18: AD conversion unit
19: signal processing unit
20: DSC
21: image processing unit
22: probe movement range determining unit
23: acceleration sensor
A1, A2: artery G1, G2: guide panel
U1, U2: ultrasound image
V1, V2, V3: popliteal vein

What is claimed is:

1. An ultrasound diagnostic apparatus that performs a compression test with respect to at least two points of a popliteal vein and a common femoral vein of a subject, the apparatus comprising:
an ultrasound probe and a processor,
wherein the processor is configured to
acquire an ultrasound image by transmitting an ultrasound beam toward the subject from the ultrasound probe,
detect the popliteal vein included in the acquired ultrasound image,
guide a user to operate the ultrasound probe to fix a position of the ultrasound probe in a case where the compression test of the popliteal vein is performed and only one popliteal vein is detected, and
guide the user to move the ultrasound probe to an upper side of a back of a knee of the subject in a case where the compression test of the popliteal vein is performed and a plurality of popliteal veins are detected.

2. The ultrasound diagnostic apparatus according to claim 1,
wherein the processor is further configure to
determine whether a movement range of the ultrasound probe by the user from a point in time when the ultrasound probe is guided to be moved to an upper side of the back of the knee of the subject is within a predetermined range, and
guide the user to move the ultrasound probe to the back of the knee of the subject in a case where the determination is made that the movement range of the ultrasound probe is beyond the predetermined movement range.

3. The ultrasound diagnostic apparatus according to claim 2,
wherein the processor is further configured to determine that the movement range of the ultrasound probe is beyond the predetermined movement range in a case where the number of frames of a plurality of the acquired ultrasound images exceeds a predetermined number of frames from a point in time when the operation of the ultrasound probe is guided such that the ultrasound probe is moved to an upper side of the back of the knee.

4. The ultrasound diagnostic apparatus according to claim 2,
wherein the processor is further configured to determine that the movement range of the ultrasound probe is beyond the predetermined movement range in a case where an elapsed time from a point in time when the operation of the ultrasound probe is guided such that the ultrasound probe is moved to an upper side of the back of the knee exceeds a predetermined time.

5. The ultrasound diagnostic apparatus according to claim 2,
wherein the ultrasound probe includes an acceleration sensor, and
the processor is further configured to
estimate a movement distance of the ultrasound probe based on an acceleration of the ultrasound probe measured by the acceleration sensor, and
determine that the movement range of the ultrasound probe from a point in time when the operation of the ultrasound probe is guided such that the ultrasound probe is moved to an upper side of the back of the knee is beyond the predetermined movement range in a case where the estimated movement distance of the ultrasound probe exceeds a predetermined distance.

6. The ultrasound diagnostic apparatus according to claim 1,
wherein the apparatus is further comprising a display device, and
the processor is further configured to cause the display device to display operation guidance on the ultrasound probe for the user.

7. An ultrasound diagnostic apparatus that performs a compression test with respect to at least two points of a popliteal vein and a common femoral vein of a subject, the apparatus comprising:
an ultrasound probe and a processor,
wherein the processor is configured to
acquire an ultrasound image by transmitting an ultrasound beam toward the subject from the ultrasound probe,
detect the popliteal vein included in the acquired ultrasound image,
guide a user to move the ultrasound probe to an upper side of a back of a knee of the subject in a case where the compression test of the popliteal vein is performed,
determine whether a movement range of the ultrasound probe by the user from a point in time when the ultrasound probe is guided to be moved to an upper side of the back of the knee of the subject is within a predetermined range, and
guide the user to move the ultrasound probe to the back of the knee of the subject in a case where the determination is made that the movement range of the ultrasound probe is beyond the predetermined movement range.

8. The ultrasound diagnostic apparatus according to claim 7,
wherein the processor is further configured to determine that the movement range of the ultrasound probe is beyond the predetermined movement range in a case where the number of frames of a plurality of the acquired ultrasound images exceeds a predetermined number of frames from a point in time when the operation of the ultrasound probe is guided such that the ultrasound probe is moved to an upper side of the back of the knee.

9. The ultrasound diagnostic apparatus according to claim 7,
wherein the processor is further configured to determine that the movement range of the ultrasound probe is beyond the predetermined movement range in a case where an elapsed time from a point in time when the operation of the ultrasound probe is guided such that the ultrasound probe is moved to an upper side of the back of the knee exceeds a predetermined time.

10. The ultrasound diagnostic apparatus according to claim 7,
wherein the ultrasound probe includes an acceleration sensor, and
the processor is further configured to
estimate a movement distance of the ultrasound probe based on an acceleration of the ultrasound probe measured by the acceleration sensor, and
determine that the movement range of the ultrasound probe from a point in time when the operation of the ultrasound probe is guided such that the ultrasound probe is moved to an upper side of the back of the knee is beyond the predetermined movement range in a case where the estimated movement distance of the ultrasound probe exceeds a predetermined distance.

11. The ultrasound diagnostic apparatus according to claim 7,
wherein the apparatus is further comprising a display device, and
the processor is further configured to cause the display device to display operation guidance on the ultrasound probe for the user.

* * * * *